United States Patent [19]

Jacobson et al.

[11] Patent Number: 5,274,121

[45] Date of Patent: Dec. 28, 1993

[54] N-METHYL-N-[4-(1-PYRROLIDINYL)-2-BUTYNYL]AMIDE CONGENERS AS MUSCARINIC AGENTS

[75] Inventors: Kenneth A. Jacobson, Silver Spring; Barton J. Bradbury, Ellicott City; Jesse Baumgold, Bethesda, all of Md.

[73] Assignee: The United States of America as represented by the Secretary of the Department of Health and Human Services, Washington, D.C.

[21] Appl. No.: 876,917

[22] Filed: Apr. 30, 1992

Related U.S. Application Data

[63] Continuation of Ser. No. 310,954, Feb. 15, 1989, abandoned.

[51] Int. Cl.[5] .............. C07D 207/08; C07D 207/46; A61K 31/40
[52] U.S. Cl. ...................... 548/568; 514/428
[58] Field of Search .................. 548/568; 514/428

[56] References Cited

U.S. PATENT DOCUMENTS 3,354,178  11/1967  Dickinson .............. 260/326.3
4,065,471  12/1977  Dickinson .............. 260/326

OTHER PUBLICATIONS

CA vol. 108, No. 3, abstract 16138K of Ringdahl, et al., J. Pharmacol. Exp. Ther. 1987, 242(2).

Bradbury, et al., "Design of Novel Muscarinic Agents", Journal of Medicinal Chemistry, Feb. 1990, pp. 741–748.

Primary Examiner—Frederick E. Waddell
Assistant Examiner—William Jarvis
Attorney, Agent, or Firm—Leydig, Voit & Mayer

[57] ABSTRACT

Compounds, which are muscarinic agents, having the formula

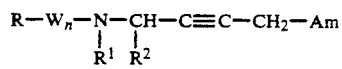

wherein
Am is $-N(R_a)_2$, $-N(R_a)_3^+ I^-$, 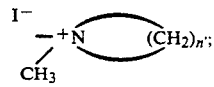 or $$I^- \atop -^+N \smile (CH_2)_{n'}; \atop CH_3$$

$n'$ is an integer from 2 to 7 and $R_a$ is an alkyl having 1 to 4 carbon atoms, and each $R_a$ may be the same or different wherein the other substituents are defined hereinbelow.

6 Claims, No Drawings

N-METHYL-N-[4-(1-PYRROLIDINYL)-2-BUTYNYL]AMIDE CONGENERS AS MUSCARINIC AGENTS

This is a continuation of application Ser. No. 07/310,954, filed on Feb. 15, 1989, which was abandoned upon the filing hereof.

This invention relates to compounds that are a series of N,N'-substituted-1,4-diamino-2-butynes, with or without a 1-alkyl substituent, that bind to muscarinic receptors. This invention also relates to a method of inducing pharmacological manifestation associated with muscarinic receptor agonist and antagonist activity by administering a safe and effective amount of the muscarinic receptor specific compounds.

BACKGROUND OF THE INVENTION

In the peripheral nervous system, all internal organs innervated by the parasympathetic nervous system have muscarinic receptors. For example, the heart, gastrointestinal tract, the urinary bladder, the sweat glands, the lacrimal glands, the blood vessels, and the pupils are all innervated through muscarinic receptors. The central nervous system is also comprised of a complex network of muscarinic receptors, both pre- and postsynaptic.

It has recently been discovered that there are several classes of muscarinic receptors based on their selectivity for certain agonists and antagonists. Molecular biological studies of muscarinic cholinergic receptors (mAChRs) have raised the possibility of designing subtupe-specific agonists and antagonists. See Bonner, T. I.; Buckley, N. J.; Young, A. C.; Brann, M. R.; *Science* 1987, 237, 527 (hereinafter Bonner); and Peralta, E. G.; Winslow, J. W.; Ashkenazi, A.; Smith, D. H.; Ramachandran, J.; Capon, D. J.; *Trends Pharm. Sci. Suppl.*, 1988, 9, 6, which are specifically incorporated by reference herein.

Complications in defining the selectivity of muscarinic ligands have developed from recent studies of the classification, regional distribution, and second messenger coupling of mAChR subtypes. Two mAChR subtypes have been defined pharmacologically on the basis of their affinities for the non-classical antagonist pirenzepine. See Giacobini, E.; Becker, R.; *Current Research in Alzheimer Therapy*, Taylor & Francis, New York, 1988 (hereinafter Giacobini), which is specifically incorporated by reference herein. One muscarinic receptor subtype, the $M_1AChRs$, have a high-affinity for pirenzepine, whereas another muscarinic receptor subtype, the $M_2AChRs$, have a low-affinity. See Giacobini. Recent work in the cloning of human mAChRs has redefined the mAChR into five new structural classes, $m_1AChR$ $m_5AChR$. See Bonner; Peralta, E. G., Winslow, J. W., Ashkenazi, A., Smith, D. H., Ramachandran, J., Capon, D. J., *Trends Pharm. Sci. Suppl.*, 1988, 9, 6 (hereinafter Peralta, *Trends*); and Peralta, E. G.; Ashkenazi, A.; Winslow, J. W.; Smith, D. H.; Ramachandran, J.; Capon, D. J.; *EMBO J.* 1987, 6,3923, Bonner, T. I.; Young, A. C.; Brann, M. R.; Buckley, N. J.; *Neuron* 1988, 1,403, which are all incorporated by reference herein. Pharmacologically, the $m_1$- and $m_4AChR$ demonstrate a high affinity for pirenzepine, $m_3$— and $m_5AChR$ have intermediate affinity, and the $m_2AChR$ has low affinity. See Peralta, *Trends*. By way of background, there has been confusion concerning the nomenclature used to describe MAChRs. The nomenclature of Peralta is used throughout, which differs from that of Bonner for the $m_3$ and $m_4AChR$, i.e. their nomenclature for these two receptors are reversed.

Recently, these subclasses of mAChRs have been defined according to their functional correlation to second messenger systems. Muscarinic receptors are known to be coupled to phosphatidylinositol (PI) turnover, adenylate cyclase, and potassium channels. See Gil, D. W.; Wolfe, B. B.; *J. Pharmacol. Exp. Ther.* 1985, 232, 608; and Yatani, A.; Codina, J.; Brown, A. M.; Birnbaumer, L. *Science* 1987, 235, 207. The $m_1$-, $m_4$-, and $m_5AChRs$ have been shown to couple exclusively to PI turnover, whereas $m_2$- and $m_3AChRs$ couple only to adenylate cyclase inhibition. See Peralta, E. G., Ashkenazi, A., Winslow, J. W., Ramachandran, J., Capon, D. J., *Nature*, 1988, 334, 434, which is specifically incorporated by reference herein.

It is believed that muscarinic agonists and antagonists that are specific for a muscarinic receptor subtype could have substantial therepeutic benefits. For example, considerable research has been devoted to studying the therapeutic benefits of central muscarinic agonists in the treatment of senile dementia of the Alzheimer's type. See Giacobini and Davidson, M., Haroutunian, V., Mohs, R. C., Davis, B. M., Horvath, T. B., Davis, K. L.; *Alzheimer's and Parkinson's Diseases: Strategies for Research and Development*, Plenum, New York, 1986, 531–537 (hereinafter Davidson), which is specifically incorporated by reference herein. Currently available therapeutic cholinergic agents suffer from serious side effects, toxicity, and narrow therepeutic windows. See Bonner and Davidson. It is believed that agonists and antagonists that are specific for muscarinic receptor subtypes would be devoid of many of these side effects.

The development of potent selective receptor ligands using the "functionalized-congener" approach to drug design has been successfully established in the field of adenosine receptor ligands and catecholamines. See Jacobson, K. A.; Kirk, K. L.; Padgett, W. L.; Daly, J. W.; *J. Med. Chem.* 1985, 28, 1334; Jacobson, K. A.; Kirk, K. L.; Padgett, W. L.; Daly, J. W.; *J. Med. Chem.* 1985, 28, 1341; and Jacobson, K. A.; Marr-Leisy, D.; Rosenkranz, R. P.; Verlander, M. S.; Melmon, K. L.; Goodman, M.; *J. Med. Chem.* 1983, 26, 429, which are specifically incorporated by reference herein. By this approach, a chain terminating in a functional group (eg., an amine or carboxylic acid) is appended to a known receptor ligand at a site which allows modification with retention of biological activity. The chain-extended functional group may enhance receptor affinity and selectivity, and serves as a site for further functionalization to develop irreversible inhibitors, prodrugs, or labeled receptor probes. See Jacobson, K. A.; In *Receptor Biochemistry and Methodology*, (Venter, J. C.; Harrison, L. C., Eds.) Vol. II *Adenosine Receptors*; Cooper, D. M. F.; Londos, C., Eds.; Alan R. Liss: New York, 1988; pp 1-26, which is specifically incorporated by reference herein. This drug design approach may be applicable to other receptor ligands, in particular, muscarinic agents.

Many muscarinic agents contain an N-(4-amino-2-butynyl)amide substructure, most notably, oxotremorine,

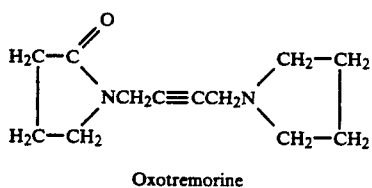

Oxotremorine a potent and moderately selective central muscarinic agonist. See Noronha-Blob, L.; Canning, B.; Costello, D.; Kinnier, W. J.; *Eur. J. Pharmacol.* 1988, 154, 161; Bebbington, A.; Brimblecombe, R. W.; Shakeshaft, D.; *Brit. J. Pharmacol.* 1966, 26, 56; Bebbington, A.; Brimblecombe, R. W.; Rowsell, D. G.; *Brit. J. Pharmacol.* 1966, 26, 68; Neumeyer, J. L.; Moyer, U. V.; Richman, J. A.; Rosenberg, F. J.; Teiger, D. G.; *J. Med. Chem.* 1967, 10, 615; and Ringdahl, B.; Jenden, J.; *Life Sci.* 1983, 32, 2401; which are specifically incorporated by reference herein. While modification of either end of the linear central chain often has profound effects on biological activity, an open-ring analogue of oxotremorine, UH 5,

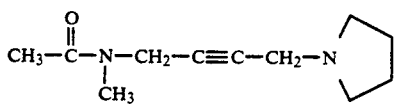

maintains agonist activity and is nearly equi-potent to oxotremorine. Related to UH 5, BM 5,

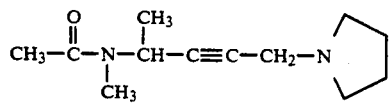

is also a potent muscarinic agent with presynaptic antagonist and postsynaptic agonist activity. See Nordström, Ö., Unden, A.; Grimm, V.; Frieder, B.; Ladinsky, H.; Bartfai, T.; In *Dynamics of Cholinergic Function*; Hanin, I., Ed.; Plenum: New York; 1983, pp 405–413; which is specifically incorporated by reference herein. This pharmacological profile is reported to be ideal for the putative treatment of Alzheimers dementia. See Hershenson, F. M.; Moos, W. H.; *J. Med. Chem.* 1986, 29, 1125; which is specifically incorporated by reference herein.

SUMMARY OF THE INVENTION

The present invention provides novel compounds which are capable of binding to muscarinic receptors. The structural nucleus of the compounds is a 2-butynamine with a substituted nitrogen at the 4-position with alkyl group variations on the 1- and 4-position nitrogen and the 1-position carbon. The novel compounds include those which function either as agonists and/or antagonists and may be used to induce pharmacological or therapeutic effects corresponding to agonist and/or antagonist activity in humans and other animals. A particularly preferred group of compounds are muscarinic receptor agonists or partial agonists and may be used in the treatment of Alzheimer's disease, or as pharmacological probes for receptor studies. Preferred compounds are designed as functionalized congeners of the 4-amino-2-butynamine parent nucleus by variable derivitization of the 1-position nitrogen.

In accordance with the present invention, there are provided compounds of the formula:

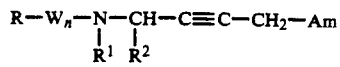

wherein

Am is $-N(R_a)_2$, $-N(R_a)_3{}^+I^-$, $-N\underset{}{(CH_2)_{n'}}$, or

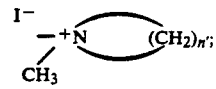

$n'$ is an integer from 2 to 7 and $R_a$ is an alkyl having 1 to 4 carbon atoms, and each $R_a$ may be the same or different;

$R^1$ and $R^2$, which may be the same or different, are hydrogen or an alkyl having 1 to 4 carbon atoms;

n is an integer from 0 to 10;

W is a group selected from any naturally occuring amino acid of the D or L configuration; $-Z-Y-X-$; $-Z-Y-$; $-Z-X-$; $-Y-X-$; $-Z-$; $-Y-$; or $-X-$; wherein:

X is $-CO-$, $-CS-$, or $-SO_2-$;

Y is a straight or branched chain alkyl having 1 to 10 carbon atoms, a dioxolone ring attached at its 2-position and substituted at its 4 position with W; a dioxolone ring attached at its 4-position and substituted at its 2 position with W; an alkylaryl or aryl, wherein the aryl is

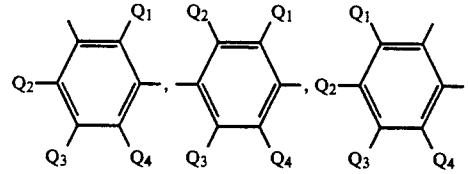

and $Q^1$-$Q^4$ can be a combination of hydrogen, halogen, $-OCH_3$, $-OH$, $-NO_2$, $-CF_3$, $-COCF_3$, $-CH_3$, or $-NH_3$;

Z is $-NH-$, $-S-$, or $-O-$;

R is hydrogen, halogen, lipid, biotin, SCN—,

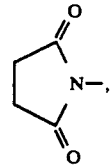

an amine protecting group, a radio labeled substituent, spin labeled substituent, or a fluorescent dye.

The compounds include agonists, antagonists and partial agonist (mixed agonist/antagonist) specific for muscarinic receptors subtypes.

The present invention is also for a process for treating Alzheimer's disease in humans by administering a safe and effective amount of an agonist with muscarinic receptor specificity as described above.

Additional objects and advantages of the invention will be set forth in part in the description which follows, and in part will be obvious from the description, or may be learned from the practice of the invention. The objects and advantages may be realized and attained by means of the instrumentalities and combinations particularly pointed out in the appended claims.

DESCRIPTION OF THE PREFERRED EMBODIMENTS

Reference will now be made in detail to the presently preferred embodiments of the invention, which together with the following examples, serve to explain the principles of the invention.

As noted above, the present invention relates to compounds of the formula:

$$R-W_n-N(R^1)-CH(R^2)-C\equiv C-CH_2-Am$$

wherein

Am is $-N(R_a)_2$, $-N(R_a)_3{}^+I^-$, 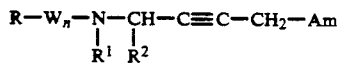, or

$n'$ is an integer from 2 to 7 and $R_a$ is an alkyl having 1 to 4 carbon atoms, and each $R_a$ may be the same or different;

$R^1$ and $R^2$, which may be the same or different, are hydrogen or an alkyl having 1 to 4 carbon atoms;

n is an integer from 0 to 10;

W is a group selected from any naturally occuring amino acid of the D or L configuration; $-Z-Y-X-$; $-Z-Y-$; $-Z-X-$; $-Y-X-$; $-Z-$: $-Y-$; or $-X-$; wherein:

X is $-CO-$, $-CS-$, or $-SO_2-$;

Y is a straight or branched chain alkyl having 1 to 10 carbon atoms, a dioxolone ring attached at its 2-position and substituted at its 4 position with W; a dioxolone ring attached at its 4-position and substituted at its 2 position with W; an alkylaryl or aryl, wherein the aryl is

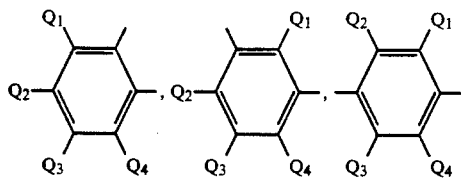

and $Q^1-Q^4$ can be a combination of hydrogen, halogen, $-OCH_3$, $-OH$, $-NO_2$, $-CF_3$, $-COCF_3$, $-CH_3$, or $-NH_3$;

Z is $-NH-$, $-S-$, or $-O-$;

R is hydrogen, halogen, lipid, biotin, SCN—,

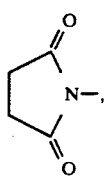

an amine protecting group, a radio labeled substituent, a spin labeled substituent, or a fluorescent dye.

Compounds of the present invention utilize as a core 2-butynamine connected to a substituted nitrogen at the 4-position with alkyl group variations on the 1-position nitrogen and the 1-position carbon. The 4-position nitrogen is disubstituted with branched or straight chain alkyl groups, or it may be incorporated into a ring of up to 8 members. The alkyl chain or ring may also be substituted, and the nitrogen may be quaternized with methyliodide.

A functionalized chain is constructed on the 1-position nitrogen through a connecting group (X) and a spacer group (Y), terminating in some readily-derivatized functional group (Z) to which the prosthetic group (R) is attached. The connecting group (X) may be: 1) $-CO-$, 2) $-CS-$, 3) $-SO_2$, or 4) nothing. The spacer group (Y) may be: 1) an alkyl chain, 2) an alkyl-aryl group 3) an aryl group, 4) a dioxolane ring attached at it's 2- or 4-position, or 5) nothing. The functional group (Z) may be: 1) $-NH-$, 2) $-S-$, 3) $-O-$, or 4) nothing. The combinaton of Z—Y—X may be repeated with the same or different combinations of Z—Y—X, before it is terminated with a prosthetic group (R) which may be: 1) hydrogen, 2) halogen, 3) a protecting group for Z such as tert-butyloxycarbonyl if Z is $-NH-$, 4) a lipid, 5) biotin, 6) strong electrophilic groups such as SCN or succinimide if Z is $-O-$, 7) a radio label such as $^{18}F$ or $^{125}I$, 8) a spin label such as tetramethyl-1-piperidinyloxy (TEMPO), or 9) a fluorecent dye such as fluoroscein. See Jacobson, K. A., Furlano, D. C., and Kirk, K. L., J. Fluor. Chem.; vol. 39; pg. 339 (1988). The functional group serves as a point of attachment for radiolabelled or other tracer groups so these compounds may be used as receptor probes for muscarinic receptors. Other functions of the prosthetic group include handles for irreversible inhibitor groups, and handles for selectively metabolized groups for the development of prodrugs.

Compounds of the present invention which are selective for muscarinic receptor subtypes are believed to have numerous therapeutic benefits. For example, compounds that are selective for the muscarinic receptors in the heart would be useful in clinical cardiology. Agonists that stimulate the muscarinic receptors of the heart would decrease the heart rate and decrease the force of cardiac contraction, whereas antagonists would have the opposite effect. Also muscarinic agonists are potent vasodilators and might be useful in the treatment of hypertension. Selective muscarinic antagonists could also be useful as antiperspirants. Compounds of the present invention would also be useful in the gastrointestinal system since agonists would increase peristaltic activity and enhance secretory activity. Muscarinic antagonists according to the present invention would produce the opposite results and might be useful in the treatment of gastric ulcers. Muscarinic agonists that are selective for receptors in the urinary tract would stimulate the urinary tract and might be useful in treating patients with neurogenic bladder.

In the central nervous system, muscarinic receptors mediate a variety of neuronal functions, including memory and certain phases of sleep. Compounds of the present invention which exhibit selective muscarinic agonist activity may be useful in treating cognitive deficits, such as in Alzheimer's disease.

Compounds of the present invention were tested for their binding affinities and activation of second messengers in selective muscarinic cholinergic receptor systems. It is believed that $m_1$-, $m_4$-, and $m_5$ AChRs couple exclusively to PI turnover, whereas $m_2$- and $m_3$-AChRs couple only to adenylate cyclase inhibition.

Compounds of the present invention were screened for their biological activity. Assay systems using SK-N-SH human neuroblastoma cells which express only $m_4$-AChRs coupled to PI turnover, and NG108-15 neuroblastoma x glioma cells which express only $m_3$AChRs coupled to adenylate cyclase inhibition were used. The results of this assay are set forth in Table I.

The results show that several of the compounds were active in inhibiting cAMP production in NG108-15 cells, indicating that these compounds are $m_3$-selective muscarinic agonists. Of the compounds tested, compounds 007 (Example III) and 017 were the most active as agonists in NG108-15 cells. These two compounds were approximately half as active as the full agonist oxotremorine-M, which inhibited cAMP formation by $65\pm3\%$ in this assay. These two compounds were inactive in SK-N-SH cells and, thus, are selective agonists. In contrast, UH5 acted as an agonist in both systems, with activities of 63% and 54% for cyclic cAMP inhibition and PI turnover, respectively. Several other compounds demonstrated substantial activity, including compounds 006, 016, 036, 039, 010, and 022. In contrast, all of the compounds tested were either inactive or only slightly active in stimulating PI turnover in SK-N-SH cells, indicating that these compounds are not active as $m_4$-specific muscarinic agonists.

Compounds of the present invention were also screened for their relative binding affinities. Assay systems which measured the inhibition of $^3$H-N-methylscopolamine ($^3$H-NMS) binding to membranes from NG108-15 cells and membranes from SK-N-SH cells were used. The results of this assay are illustrated in Table I.

These results show that all of the compounds tested had some activity in binding to muscarinic receptors. Compounds 045, 043, 047, and 046 were the most active in this regard. Since these compounds were inactive as agonists, their binding activity is attributable to their activity as antagonists in these assays. None of the compounds tested exhibited any substantial selectivity as antagonists, since their activity in inhibiting $^3$H-NMS binding from membranes from each cell line is approximately similar.

Preparation of compounds within the scope of the present invention appear in the following examples.

EXAMPLES

The following general procedures were used in the preparation of the compounds described in the examples. All melting points were determined on a Thomas Hoover Uni-Melt apparatus and are uncorrected. All $^1$H NMR spectra were recorded using a Varian XL-300 FT-NMR spectrometer and all values are reported in parts per million (ppm, δ) downfield from tetramethylsilane (TMS). Chemical ionization MS using ionized NH$_3$ gas were recorded using a Finnigan 1015D mass spectrometer modified with EXTREL electronics. IR spectra were recorded on a Beckman 4230 IR spectrophotometer. Thin-layer chromatography (TLC) analyses were carried out using Analtech 250 μ silica gel GF 'Uniplates' or EM Kieselgel 60 F254, DC-Alufolien 200 μplates. Silica gel columns used MN-Kieselgel 60, 0.063″ 0.2 mm silica gel. Elemental analyses were performed by Atlantic Microlab, Inc., Atlanta, Ga. The term in vacuo refers to a vacuum provided by a water aspirated (15-30 mm Hg) rotary-evaporator, high vacuum refers to a vacuum of 0.05-0.5. Percent yields are rounded to the nearest whole number. An asterix (*) for the $^1$H NMR data indicates the higher-integration signal for the pair of signals which represent the same proton(s) of the amide tautomers. A carat (^) for the $^1$H NMR data indicates signals whose assignments are ambiguous. Stock solutions (10 or 20 mM) of the ½-oxalate salts of the compounds in H$_2$O were stored at $-20°$ C. until used for pharmacological testing.

EXAMPLE I

Preparation of N-Methyl-4-(1-pyrrolidinyl)-2-butynamine. (004)

Di-tert-butyldicarbonate (27.0 mL, 117 mmol) was slowly added to a stirring solution of N-methylpropargylamine (10.0 mL, 118 mmol) at 25° C. The mixture was allowed to stir for 1 h or until complete by TLC analysis. All volatiles were removed in vacuo to yield 19.2 g (97%) of the crude Boc-N-methypropargylamine as a light yellow oil: MS (CI-NH$_3$) m/e 186 (M-NH$_3$+) 170 (MH+), 86 (base); $^1$H NMR (CDCl$_3$) δ1.46 (s, 9 H), 2.20 (s, 1 H), 2.90 (s, 3 H), 4.03 (br s, 2 H). This oil (16.9 g, 100 mmol) was then dissolved in 200 mL of dioxane. To this solution was added pyrrolidine (10.4 mL, 125 mmol), paraformaldehyde (3.8 g, 125 mmol), and a catalytic amount of CuCl (400 mg, 4 mmol). The mixture was allowed to react for 4 h at 25° C. and then it was stirred at 50° C. for 1 h. The mixture was then cooled to 25° C., poured into a 6M citric acid solution (100 mL), and washed with CH$_2$Cl$_2$ (3×50 mL). The product was made basic (pH 10) with Na$_2$CO$_3$ and the product was extracted into CH$_2$Cl$_2$ (3×100 mL). All volatiles were removed in vacuo to give 23.0 g (91%) of crude Boc-N-methyl-4-(1-pyrrolidinyl)-2-butynamine as a yellow oil: MS (CI—NH$_3$) m/e 253 (MH+), 197, 153 (base); $^1$H NMR (CDCl$_3$), δ1.44 (s, 9 H), 1.78 (br s, 4 H), 2.58 (br s, 4 H), 2.88 (s, 3 H), 3.38 (s, 2 H), 4.03 (br s, 2 H). This crude oil was then cooled to 0° C. and excess TFA ($\approx$50 mL) was slowly added with stirring. The excess TFA was removed in vacuo, and 2 M Na$_2$CO$_3$ was added until basic (pH 10). The crude diamine was extracted into CH$_2$Cl$_2$ (3×100 mL), and then vacuum distilled to give 9.0 g (66%, 57% from N-methylpropargylamine) of N-Methyl-4-(1-pyrrolidinyl)-2-butynamine as a clear, colorless oil: bp 50° C. (0.1 mm Hg); MS (CI-NH$_3$) m/e 153 (MH+); $^1$H NMR (CDCl$_3$),δ1.63 (br s, 1 H, exc) 1.79 (br s, 4 H), 2.46 (s, 3 H), 2.59 (br s, 4 H), 3.40 (s, 4 H); IR (neat) 3280, 2980, 2800, 1450, 1350, 1325, 1125 cm$^{-1}$.

The following general coupling procedure was used in the preparation of compounds according to the claimed invention. To a solution of the appropriate Boc-protected amino acid in MeCN was added 1.1 eq of DCC. The mixture was stirred for 15 min at 25° C. before a solution of 0.75 eq of N-methyl-4-(1-pyrrolidinyl)-2-butynamine in MeCN was slowly added. After 4 h, or until complete by TLC (more Boc-amino acid and DCC was added if necessary), the suspension was filtered. The filtrate was evaporated in vacuo and then redissolved in EtOAc and washed with 2M Na$_2$CO$_3$ (3× equal volume). The product was then extracted into a 6M citric acid solution and washed with CH$_2$Cl$_2$ (3× equal volume). The acidic aqueous layer was made basic (pH 10) with solid Na$_2$CO$_3$ or 4N NaOH and the product was extracted into CH$_2$Cl$_2$. The organic phase was then dried over Na$_2$SO$_4$ and evaporated in vacuo to give the corresponding Boc-amino acid congener.

EXAMPLE II

Preparation of N-Methyl-N-[4-(1-pyrrolidinyl)-2-butynyl]-2-(N-Boc-amino) acetamide. (006)

TLC (CHCl$_3$/MeOH/NH$_4$OH, 40/10/1), R$_f$ 0.67; $^1$H NMR (CDCl$_3$) δ1.39 (s, 9 H), 1.74 (br s, 4 H), 2.52 (br s, 4 H), 2.95 (s, 3 H), 3.32 (s, 2 H), 3.88* & 3.97^ (s, 2 H), 3.94 ^ & 4.20* (s, 2 H). Anal. Calcd for C$_{16}$H$_{27}$N$_3$O$_3$: C, 62.11; H, 8.80; N, 13.58. Found: C, 62.14; H, 8.83; N, 13.54.

The following general deblocking procedure was used in the preparation of compounds according to the claimed invention.

Excess TFA was added slowly to the neat Boc-protected congener, such as N-Methyl-N-[4-(1-pyrrolidinyl)-2-butynyl]-2-(N-Boc-amino)acetamide, and stirred for 1 h or until complete by TLC. The excess TFA was removed in vacuo to give the ditrifluoroacetate salt of the corresponding amino amide.

EXAMPLE III

Preparation of N-Methyl-N-[4-(1-pyrrolidinyl)-2-butynyl]-2-aminoacetamide (007).

TLC (CHCl$_3$/MeOH/TEA: 15/10/1), R$_f$ 0.53; MS (CI-NH$_3$), m/e 210 (MH+); $^1$H NMR (CDCl$_3$ δ1.73 (s, 3 H [2 N-H's and ½H$_2$O]), 1.79 (br s, 4 H), 2.58 (br s, 4 H), 2.98* & 3.00 (s, 3 H), 3.38 (s, 2 H), 3.43* & 3.51 (s, 2 H), 3.98 & 4.26 (s, 2 H). Anal. Calcd for C$_{11}$H$_{19}$N$_3$O: C, 63.13; H, 9.15; N, 20.08.

The following general procedure was used for N-Acetylation of compounds according to the present invention. The ditrifluoroacetate diamine, such as N-Methyl-N-[4-(1-pyrrolidinyl)-2-butynyl]-2-aminoacetamide ditrifluoracetate, was stirred in MeCN with 3.1 eq of triethylamine and 1.1 eq of Ac$_2$O. After 15 min, or until complete by TLC, the MeCN was removed under a stream of N$_2$, the residue was dissolved in EtOAc, and washed with 2M Na$_2$CO$_3$ saturated with NaCl (3× equal volume). The organic phase was dried over Na$_2$SO$_4$ and all volatiles were removed in vacuo to give the corresponding N-acetylamino congeners.

EXAMPLE IV

Preparation of N-Methyl-N-[4-(1-pyrrolidinyl)-2-butynyl]-2-(N- acetylamino) acetamide (010).

TLC (CHCl$_3$/MeOH/NH$_4$OH, 10/10/1), R$_f$0.60;MS (CI-NH$_3$), m/e 252 (MH+); $^1$H NMR (CDCl$_3$) δ1.80 (br s, 4 H), 2.04 (s, 3 H), 2.56 (br s, 4 H), 3.03 (s, 3 H), 3.38 (s, 2 H), 4.03* & 4.12 ^ (t, J=3.8 Hz, 2 H), 4.13^ & 4.26* (s, 2 H), 6.56 (br s, 1 H). Anal. Calcd for C$_{13}$H$_{21}$N$_3$O$_2$: C, 62.13; H, 8.42; N, 16.72.

EXAMPLE V

Preparation of N-Methyl-N-[4-(1-pyrrolidinyl)-2-butynyl]-3-carboxypropanamide (008).

Intermediate compound 004 (557 mg, 3.66 mmol) was added to a solution of succinic anhydride (330 mg, 3.30 mmol) and triethylamine (20.51 mL, 3.66 mmol) in MeCN was removed under a stream of N$_2$, and the crude product was chromatographed on a silica gel column (CHCl$_3$/MeOH/AcOH, 10/10/1) to give N-Methyl-N-[4-(1-pyrrolidinyl)-2-butynyl]-3-carboxypropanamide as a light brown solid. MS (CI-NH$_3$), m/e 253 (MH+); TLC (CHCl$_3$/MeOH/AcOH: 10/10/1), R$_f$ 0.34; $^1$H NMR (CDCl$_3$) δ1.82 (br s, 4 H), 2.48 (t, J=5.8 Hz, 2 H), (t, J=5.8 Hz, 2 H), 2.68 (br s, 4 H), 2.93 & 3.06* (s, 3 H), 3.44 (s, 2 H), 4.11 & 4.21* (s, 2 H).

EXAMPLE VI

Preparation of N-Methyl-N-[4-(1-pyrrolidinyl)-2-butynyl]-3-methoxycarbonylpropanamide (009).

Dowex 50 resin (200 mg) which had been activated with HCl was added to a solution of N-Methyl-N-[4-(1-pyrrolidinyl)-2-butynyl]-3-carboxypropanamide (101 mg, 0.40 mmol) in MeOH (2 mL) and the suspension was vigorously stirred overnight. The resin was filtered off and washed thoroughly with TFA. The combined MeOH and TFA washes were evaporated under a stream of N$_2$, neutralized with 2M Na$_2$CO$_3$ solution and the product was extracted into EtOAc (3× mL). The organic layer was dried over Na$_2$CO$_3$, evaporated in vacuo and purified on silica gel (CHCl$_3$/MeOH/N-H$_4$OH, 40/10/1) to give 009 (66.8 mg, 63% yield). MS (CI-NH$_3$), m/e 267 (MH+), 186, 172. $^1$H NMR (CDCl$_3$) δ1.79 (br s, 4 H), 2.58 (br s, 4 H), 2.64 (m, 4 H), 2.98 & 3.07* (s, 3 H), 3.38 (s, 2 H), 3.68 (s, 3 H), 4.08 & 4.24* (s, 2 H).

EXAMPLE VII

Preparation of N-Methyl-N-[4-(1-pyrrolidinyl)-2-butynyl]-2-[4-(2-aminoethyl)carboxamido]propanamide (019).

Excess ethylenediamine (ED) was added to N-Methyl-N-[4-(1-pyrrolidinyl)-2-butynyl]-3-methoxycarbonylpropanamide and heated at 50° C. for 4 h. The excess ED was removed under a stream of N$_2$ (purified) to give N-Methyl-N-[4-(1-pyrrolidinyl)-2-butynyl]-2-[N-(2-aminoethyl) carboxamido]-propanamide. MS (CI/NH$_3$) m/e 295 (MH+), 203 (base), 143; $^1$H NMR (CDCl$_3$) δ1.73 (br s, 4 H), 2.08 (br s, 3 H), 2.47 (t, J=6.2 Hz, 2 H), 2.52 (br s, 4 H), 2.62* & 2.69 (t, J=6.2 Hz, 2 H), 2.75 (t, J=5.8 Hz, 2 H), 3.23 (dt, J=5.8, 6.0 Hz, 2 H), 3.31 (s, 2 H), 3.31 (s, 2 H), 2.91 & 3.00* (s, 3 H), 4.03 & 4.15(s, 2 H), 6.45 (br s, 1 H).

EXAMPLE VIII

Preparation of N-Methyl-N-[4-(1-pyrrolidinyl)-2-butynyl]-2-[N-(2-[N-acetylamino]ethyl)carboxamido]-propanamide (023).

Acetylation of N-Methyl-N-[4-(1-pyrrolidinyl)-2-butynyl]-2-[N-(2-aminoethyl)carboxamido]propanamide according to the general procedure vide supra to gave N-Methyl-N-[4-(1-pyrrolidinyl)-2-butynyl]-2-[N-(2-[N-acetylamino]ethyl)carboxamido]propanamide. MS (CI-NH$_3$), m/e 337 (MH+), 268, 185; $^1$H NMR (CDCl$_3$) δ1.80 (br s, 4 H), 1.98 (s, 3 H), 2.47 (t, J=Hz, 2 H), 2.58 (br s, 4 H), 2.70* & 2.78 (t, J=6.2 Hz, 2 H), 2.98 & 3.08* (s, 3 H), 3.37 (br s, 6 H), 4.10 & 4.23* (s, 2 H), 6.51 (br s, 1 H), 6.68 (br s, 1 H).

EXAMPLE IX

Preparation of N-(2,5-dioxolylmethyl)-N-methyl-4-(1-pyrrolidinyl)-2-butynamine (029).

A solution of N-Methyl-4-(1-pyrrolidinyl)-2-butynamine (83.4 mg, 0.548 mmol), TEA (153 μL, 1.098 mmol), HMPA (114 μL, 0.657 mmol), and 2-(bromomethyl)-1,3-dioxolane (68 μL, 0.657 mmol) in DMF (2 mL) was stirred at 50 ° C. for 20 h or until complete by TLC. The mixture was poured into EtOAc (20 mL) then washed with 1N NaOH saturated with NaCl (3×20 mL). The organic layer was dried over Na$_2$SO$_4$, and the EtOAc removed in vacuo to give a crude orange oil (102.8 mg, 79% yield). This oil was vacuum distilled to give N-(2,5-dioxolylmethyl)-N-methyl-4-(1-pyrrolidinyl)-2-butynamine as a clear oil: bp 90° C. (0.2 mm Hg); MS (CI-NH$_3$), m/e 239 (MH+); $^1$H NMR (CDCl$_3$) δ1.74 (br s, 4 H), 2.33 (s, 3 H), 2.58 (br H), 3.37 (s, 2 H), 3.38 (s, 2 H), 3.79 (m, 2 H), 3.92 (m, 2 H), 4.90 (t, J=4.6 Hz, 1 H).

The following general procedure was used for N-benzoylation of compounds according to the present invention. The ditrifluoroacetate diamine, such as N-Methyl-N-[4-(1-pyrrolidinyl)-2-butynyl]-2-aminoacetamide ditrifluoracetate, was stirred in MeCN with 3.1 eq of triethylamine and 1.1 eq of benzoyl chloride. After 15 min, or until complete by TLC, the MeCN was removed under a stream of N$_2$, the residue was dissolved in EtOAc, and washed with 2M Na$_2$CO$_3$ saturated with NaCl (3× equal volume). The organic phase was dried over Na$_2$SO$_4$ and all volatiles were removed from in vacuo to give the corresponding N-benzoylylamino congeners.

EXAMPLE X

Preparation of N-Methyl-N-[4-(1-pyrrolidinyl)-2-butynyl]-5-(N-benzoylamino)butanamide (055).

TLC (CHCl$_3$/MeOH/NH$_4$OH, 40/10/1) R$_f$0.53; $^1$H NMR (CDCl$_3$) δ1.74 (br s, 4 H), 1.97 (m, 2 H), 2.43* & á (t, J=6.3 Hz, 2 H), 2.53á (br m, 4 H), 2.92 & 2.99* (s, 3 H), 3.30 (s, 2 H), 3.44 (dt, J=5.1, 7.2 Hz, 2 H), 3.99 & 4.18* (s, 2 H), 7.20 (s, 1 H), 7.26 (br s, 1 H), 7.38 (m, 2 H), 7.76 (d, J=8.1 Hz, 2 H). [áOverlapping triplet and broad singlet]; MS (CI-NH$_3$) m/e 342 (MH+), 273, 121.

EXAMPLE XI

Preparation of N-Methyl-N-[4-(1-pyrrolidinyl)-2-butynyl]-5-(N-[2-(N-Boc-amino)ethanoyl]amino)-butanami de (052).

Prepared using the general procedure for DCC coupling. TLC (CHCl$_3$/MeOH/NH$_4$OH, 40/10/1) R$_f$0.41; $^1$H NMR(CDCl$_3$) δ1.45 (s, 9 H), 1.82 (br s, 4 H), 1.89 (m, 2 H), 2.39* & 2.46 (t, J=6.7 Hz, 2 H), 2.61 (br s, 4 H), 2.98 & 3.04* (s, 3 H), 3.32 (dt, J=6.0, 6.3 Hz, 2 H), 3.40 (s, 2 H), 3.76 (d, J=5.7 Hz, 2 H), 4.04 & 4.24* (s, 2 H), 5.23 & 5.46* (br s, 1 H), 6.71 (br s, 1 H); MS (CI-NH$_3$) m/e 395 (MH ), 321, 295 (base), 121

Stimulation of PI turnover in SK-N-SH cells

Cells were plated into 24-well plates at 100,000 cells per well. After 24 hours, they were labeled overnight with 2 μCi per well of [$^3$H]-myo-inositol (American Radiolabeled Chemicals, Inc., St. Louis, Mo.; 15 Ci/mM; 2 μL of stock per mL of media). The cells were then rinsed twice with 10 mM LiCl in DMEM-Hepes and the cells were incubated in this solution for 5 min at 37° C. The indicated compound was then added at a final concentration of 100 μM and the cells were incubated for another 30 min at 37° C. The reaction was stopped by aspirating the solution and adding cold methanol to the cells. After transferring the cells to a glass tube and sonicating briefly, chloroform and water were added to make a two-phase system. The upper aqueous phase was applied to 0.6 mL anion exchange columns (AG X8, Bio-Rad) and the columns were washed and total inositol phosphates were eluted with 1M ammonium formate and 0.1M formic acid.

Inhibition of PGE$_1$-stimulated cAMP levels in NG108-15 cells

Cells were plated in 24-well plates and were grown to 90% confluence. The growth media was then replaced with a solution of 1 mM IBMX in DMEM-Hepes (0.5 mL per well) and the cells were incubated for 10 min at 37° C. Agonists were then added at a final concentration of 100 μM, along with PGE$_1$ (final conc, 5 μM), and the cells were incubated for a further 15 min at 37° C. The reaction Was terminated by aspirating the solution and adding 0.5 mL of 0.1N HCl. In order to extract the cAMP from the cells, they were incubated in 0.1 N HCl for 30 min at room temperature. An aliquot (35 50 μL) was removed, lyophilized, and assayed for cAMP by radioimmunoassay.

Inhibition of [$^3$H]-NMS binding

Cells were grown to confluence, harvested, and a crude membrane fraction was obtained. An aliquot of the membrane fraction (150-300 μg of protein) was incubated for 90 min at 37° C. with 0.5 nM [$^3$H]-NMS and 100 μM of agonist in DMEM-Hepes. The total volume was 1 mL. The incubation was terminated by rapid filtration over GF/B filters using a Brandel cell harvester. The filters were washed three times with ice-cold 0.9% NaCl, equilibrated in scintillation counting fluid and counted on a Beckman LS 5801 liquid scintillation counter at 47% efficiency. Non-specific binding was determined by coincubation with 1 μM atropine, and amounted to less than 15% of total counts. It was routinely subtracted from the total counts.

It will be apparent to those skilled in the art that various modifications and variations can be made in the processes and products of the present invention. Thus, it is intended that the present invention cover the modifications and variations of this invention provided they come within the scope of the appended claims and their equivalents.

TABLE I

Biological activity and binding affinity of N-methyl-N-[4-(1-pyrrolidinyl)-2-butynyl] amide congeners

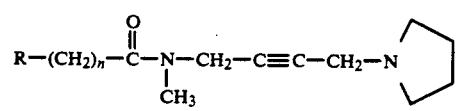

| | Compounds[a] | | NG108-15 cells | | SK-N-SH cells | |
|---|---|---|---|---|---|---|
| No. | n | R | cAMP Inhib[b] | binding[c] | Pi turnover[d] | binding[c] |
| OXO-M | — | — | 64.1 ± 1.9 | 96.2 ± 2.1 | 100 | 52.1 ± 1.2 |
| BM 5 | — | — | — | 97.0 ± 2.0 | — | 99.0 ± 1.0 |
| UH 5 | — | — | 63.2 ± 6.0 | — | — | — |
| 006 | 1 | NHBoc | 7.0 ± 2.9 | 32.6 ± 1.5 | i | 40.0 ± 2.1 |
| 007 | 1 | NH$_2$ | 26.1 ± 1.6 | 23.5 ± 4.0 | i | 17.3 ± 3.3 |
| 010 | 1 | NHAc | 14.1 ± 2.3 | 24.0 ± 5.4 | 8 ± 3 | 12.5 ± 2.8 |
| 016 | 2 | NHBoc | 12.5 ± 2.7 | 36.3 ± 3.1 | i | 45.1 ± 2.5 |
| 017 | 2 | NH$_2$ | 20.8 ± 1.7 | 15.1 ± 3.5 | i | 18.1 ± 2.8 |

TABLE I-continued
Biological activity and binding affinity of N-methyl-N-[4-(1-pyrrolidinyl)-2-butynyl] amide congeners

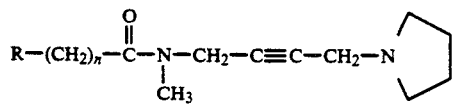

| Compounds[a] | | | NG108-15 cells | | SK-N-SH cells | |
|---|---|---|---|---|---|---|
| No. | n | R | cAMP Inhib[b] | binding[c] | Pi turnover[d] | binding[c] |
| 018 | 2 | NHAc | 10.2 ± 4.8 | 67.7 ± 3.6 | i | 67.4 ± 3.3 |
| 020 | 3 | NHBoc | 3.5 ± 1.7 | 24.4 ± 2.5 | i | 32.1 ± 0.7 |
| 021 | 3 | $NH_2$ | 3.7 ± 2.0 | 12.1 ± 2.2 | i | 20.0 ± 1.5 |
| 022 | 3 | NHAc | 8.0 ± 3.7 | 19.1 ± 1.8 | 14 ± 5 | 15.6 ± 1.6 |
| 055 | 3 | NHBzl | 0 | 16 | — | 27 |
| 035 | 4 | NHBoc | 0.5 ± 0.3 | 26.7 ± 1.6 | 1 ± 1 | 32.1 ± 2.1 |
| 036 | 4 | $NH_2$ | 15.8 ± 2.7 | 22.4 ± 3.2 | i | 34.4 ± 0.3 |
| 040 | 4 | NHAc | 5.2 ± 2.2 | 17.9 ± 7.9 | i | 29.4 ± 1.0 |
| 038 | 5 | NHBoc | 0 | 31.9 ± 0.9 | i | 39.1 ± 2.4 |
| 039 | 5 | $NH_2$ | 14.3 ± 1.0 | 37.9 ± 3.2 | i | 55.6 ± 1.9 |
| 041 | 5 | NHAc | 3.0 ± 1.7 | 22.7 ± 2.8 | 1 ± 1 | 17.4 ± 3.6 |
| 054 | 5 | NHBzl | 0 | 35 | — | 49 |
| 045 | 6 | NHBoc | 0 | 77.9 ± 2.4 | — | 81.4 ± 2.4 |
| 047 | 6 | $NH_2$ | 3.0 ± 1.2 | 72.1 ± 2.7 | — | 81.9 ± 1.0 |
| 049 | 6 | NHAc | 6.9 ± 2.9 | 20.4 ± 5.5 | — | 24.6 ± 3.1 |
| 043 | 7 | NHBoc | 0 | 89.0 ± 2.5 | — | 92.1 ± 1.0 |
| 046 | 7 | $NH_2$ | 0 | 92.3 ± 3.2 | — | 93.7 ± 1.8 |
| 048 | 7 | NHAc | 0 | 50.4 ± 4.9 | — | 59.1 ± 0.8 |
| 052 | 3 | $NHCOCH_2NHBoc$ | 0 | 5 | — | 40 |
| 053 | 3 | $NHCO(CH_2)_2NHBoc$ | 0 | 23 | — | 40 |
| 050 | 5 | $NHCOCH_2NHBoc$ | 0 | 51 | — | 50 |
| 051 | 5 | $NHCO(CH_2)_2NHBoc$ | 0 | 51 | — | 60 |

[a] stock solutions (10 or 20 mM) of each compound were made in $H_2O$ and stored at −20° C. until used.
[b] data relative to control with no compounds added, conc. of compounds = 100 μM.
[c] data expressed as % inhibition of $^3H$-NMS binding, conc. of compounds = 100 μM.
[d] data expressed as a percent relative to the activity of OXO-M, conc. of compounds = 100 μM.
i = inactive; — = not tested.

TABLE II
Biological activity and binding affinity of N-methyl-N-[4-(1-pyrrolidinyl)-2-butynyl] amide congners.

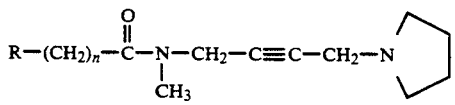

| Compounds[a] | | | NG108-15 cells | | SK-N-SH cells | |
|---|---|---|---|---|---|---|
| No. | n | R | cAMP Inhib[b] | binding[c] | Pi turnover[d] | binding[c] |
| OXO-M | — | — | 1 | 74 ± 3 | 1 | 49 ± 12 |
| BM 5 | — | — | — | 91 ± 1 | — | 95 ± 1 |
| UH 5 | — | — | — | — | — | — |
| 008 | 2 | $CO_2H$ | 0.1 ± 0.1 | 1 ± 1 | i | 7 ± 2 |
| 009 | 2 | $CO_2Me$ | 0.1 ± 0.1 | 5 ± 3 | i | 8 ± 1 |
| 019 | 2 | $CONH(CH_2)_2NH_2$ | 0.1 ± 0.1 | 14 ± 2 | i | 25 ± 5 |
| 023 | 2 | $CONH(CH_2)_2NHAc$ | 0.2 ± 0.1 | 6 ± 4 | 0.06 ± 0.04 | 6 ± 5 |
| 029 | [e] | $CH_2$-2-(1,3-dioxolyl) | 0.4 ± 0.1 | 5 ± 5 | i | 19 ± 5 |
| 031 | [e] | $(CH_2)_2$-2-(1,3-dioxolyl) | 0.5 ± 0.1 | 7 ± 5 | i | 20 ± 3 |
| 032 | 0 | $C_6H_5$ | 0.5 ± 0.2 | 7 ± 4 | 0.04 ± 0.02 | 20 ± 5 |
| 026 | 0 | $C_6H_4$-m-Cl | 0.3 ± 0.1 | 17 ± 4 | 0.01 ± 0.01 | 27 ± 10 |
| 027 | 0 | $O-C_6H_4$-p-Cl | 0.4 ± 0.1 | 27 ± 4 | 0.01 ± 0.01 | 62 ± 1 |
| 028 | 0 | $NH-C_6H_4$-p-OMe | 0.2 ± 0.1 | 24 ± 6 | i | 61 ± 12 |

[a] stock solutions (10 or 20 mM) of each compound were made in 50% ethanol and stored at −20° C. until used.
[b] data relative to OXO-M, conc. of compounds = 50 μM.
[c] data expressed as % inhibition of $^3H$-NMS binding, conc. of compound = 50 μM.
[d] data relative to OXO-M, conc. of compounds = 100 μM.
[e] carbonyl is absent, n = 0, R group attached directly to nitrogen.

What is claimed is:

1. A compound having the formula

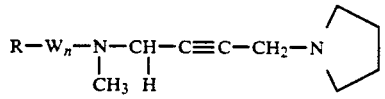

wherein
- $W_n$ is —Y—X— with X being —CO— and Y being a straight chain alkyl group having 1 to 7 carbon atoms; and
- R is NHCOOC(CH$_3$)$_3$, NH$_2$, NHCOCH$_3$, NHCOC$_6$H$_5$, NHCOCH$_2$NHCOOC(CH$_3$)$_3$ or NHCO(CH$_2$)$_2$NHCOOC(CH$_3$)$_3$.

2. The compound of claim 1, wherein R is NHCOOC(CH$_3$)$_3$.

3. The compound of claim 1, wherein R is NH$_2$.

4. The compound of claim 1, wherein R is NHCOCH$_3$.

5. The compound of claim 1, wherein R is NHCOC$_6$H$_5$.

6. The compound N-Methyl-N-[4-(1-pyrrolidinyl)-2-butynyl]-2-[N-(2-aminoethyl) carboxamido]propanamide.

* * * * *